US011654305B2

United States Patent
Benali

(10) Patent No.: US 11,654,305 B2
(45) Date of Patent: May 23, 2023

(54) PATIENT-POSITIONING DEVICE AND MEDICAL WORKSTATION

(71) Applicant: KUKA Deutschland GmbH, Augsburg (DE)

(72) Inventor: Zoubir Benali, Augsburg (DE)

(73) Assignee: KUKA Deutschland GmbH, Augsburg (DE)

( * ) Notice: Subject to any disclaimer, the term of this patent is extended or adjusted under 35 U.S.C. 154(b) by 1175 days.

(21) Appl. No.: 16/310,313

(22) PCT Filed: Jun. 9, 2017

(86) PCT No.: PCT/EP2017/064184
§ 371 (c)(1),
(2) Date: Dec. 14, 2018

(87) PCT Pub. No.: WO2017/216073
PCT Pub. Date: Dec. 21, 2017

(65) Prior Publication Data
US 2019/0255359 A1  Aug. 22, 2019

(30) Foreign Application Priority Data
Jun. 14, 2016 (DE) .................. 10 2016 210 497.7

(51) Int. Cl.
*A61N 5/10* (2006.01)
*A61G 13/04* (2006.01)
(Continued)

(52) U.S. Cl.
CPC .......... *A61N 5/1069* (2013.01); *A61G 13/04* (2013.01); *A61G 13/06* (2013.01); *A61B 6/0487* (2020.08);
(Continued)

(58) Field of Classification Search
CPC ...... A61B 6/0487; A61B 34/30; A61G 13/04; A61G 13/06; A61N 5/1049; A61N 5/1069; B25J 15/0019
See application file for complete search history.

(56) References Cited

U.S. PATENT DOCUMENTS 5,149,074 A * 9/1992 Jarin .................. A61B 6/04
5/601
5,410,767 A * 5/1995 Barud ................. A61B 6/04
5/601

(Continued)

FOREIGN PATENT DOCUMENTS

DE  102005012700 A1  9/2006
DE  102010043421 B4  7/2013
(Continued)

OTHER PUBLICATIONS

European Patent Office; Search Report and Written Opinion in related International Patent Application No. PCT/EP2017/064184 dated Aug. 14, 2017; 10 pages.
(Continued)

*Primary Examiner* — David R Hare
(74) *Attorney, Agent, or Firm* — Dorton & Willis, LLP

(57) ABSTRACT

A patient-positioning device and a medical workstation including the patient-positioning device. The patient-positioning device includes a patient couch and a robot arm which is provided for moving the patient couch and which comprises several links arranged one after another and mounted rotatably with respect to axes. The robot arm includes, as links, a start link, a first link, a second link, a third link, a fourth link, a fifth link and a sixth link. The robot arm comprises a patient couch or a fastening device on which the patient couch is fastened.

10 Claims, 3 Drawing Sheets

(51) Int. Cl.
    *A61G 13/06*     (2006.01)
    *B25J 15/00*     (2006.01)
    *A61B 34/30*     (2016.01)
    *A61B 6/04*     (2006.01)

(52) U.S. Cl.
    CPC ............ *A61B 34/30* (2016.02); *A61N 5/1049* (2013.01); *A61N 2005/109* (2013.01); *A61N 2005/1074* (2013.01); *A61N 2005/1087* (2013.01); *A61N 2005/1089* (2013.01); *B25J 15/0019* (2013.01)

(56) References Cited

U.S. PATENT DOCUMENTS

| | | | | |
|---|---|---|---|---|
| 6,126,381 | A * | 10/2000 | Bacchi | H01L 21/67766 414/754 |
| 7,860,550 | B2 * | 12/2010 | Saracen | A61B 6/548 5/601 |
| 9,076,829 | B2 * | 7/2015 | Brodine | B25J 9/042 |
| 10,368,949 | B2 * | 8/2019 | Giulianotti | A61F 5/37 |
| 11,083,420 | B2 * | 8/2021 | Suga | A61B 6/0407 |
| 11,185,456 | B2 * | 11/2021 | Hiratsuka | A61B 90/50 |
| 2005/0234327 | A1 * | 10/2005 | Saracen | A61B 6/4458 600/407 |
| 2008/0240363 | A1 | 10/2008 | Grebner et al. | |
| 2008/0301872 | A1 * | 12/2008 | Fahrig | A61B 6/0487 5/81.1 R |
| 2009/0070936 | A1 * | 3/2009 | Henderson | B25J 15/04 5/601 |
| 2010/0069920 | A1 * | 3/2010 | Naylor | A61B 34/71 606/130 |
| 2010/0275927 | A1 * | 11/2010 | Saracen | A61B 6/0487 128/845 |
| 2011/0066278 | A1 * | 3/2011 | Pinault | A61N 5/1049 414/754 |
| 2013/0025055 | A1 | 1/2013 | Saracen | |
| 2015/0327818 | A1 * | 11/2015 | Buck | A61G 13/04 5/608 |

FOREIGN PATENT DOCUMENTS

| | | | |
|---|---|---|---|
| EP | 2944259 A1 | 11/2015 | |
| WO | WO-2007025936 A1 * | 3/2007 | ........... A61B 6/0457 |

OTHER PUBLICATIONS

German Patent Office; Search Report in related German Patent Application No. 10 2016 210 497.7 dated Feb. 17, 2017; 8 pages.

* cited by examiner

PATIENT-POSITIONING DEVICE AND
MEDICAL WORKSTATION

CROSS-REFERENCE TO RELATED APPLICATIONS

This application is a national phase application under 35 U.S.C. § 371 of International Patent Application No. PCT/EP2017/064184, filed Jun. 9, 2017 (pending), which claims the benefit of priority to German Patent Application No. DE 10 2016 210 497.7, filed Jun. 14, 2016, the disclosures of which are incorporated by reference herein in their entirety.

TECHNICAL FIELD

The invention relates to a patient-positioning device, which comprises a robot arm and a patient couch, and a medical workstation comprising the patient-positioning device.

BACKGROUND

DE 10 2010 043 421 B4 discloses a medical workstation featuring a device to produce highly energized ionizing radiation to irradiate an area of a living being, a mounting device to mount a living being on and a robot arm. The robot arm is part of a robot and comprises a fastening device to which the mounting device is fastened.

SUMMARY

One object of the invention is to provide a patient-positioning device with an improved robot arm.

A further object of the invention is to provide a medical workstation with such a patient-positioning device.

The object of the invention is fulfilled by a patient-positioning device featuring a patient couch and a robot arm provided for moving the patient couch and which comprises several links arranged one after another and mounted rotatably with respect to axes, wherein the robot arm comprises, as links, a start link, a first link, a second link, a third link, a fourth link, a fifth link and a sixth link, wherein the first link is mounted rotatably in the area of one its two ends relative to a first vertical axis with respect to the start link, the first link is mounted rotatably in the area of its other end relative to a second vertical axis in the area of one of the two ends of the second link with respect to the second link, the second link is mounted rotatably in the area of its other end relative to a third vertical axis in the area of one of the two ends of the third link with respect to the third link, the fourth link is mounted rotatably in the area of one of its ends relative to a first horizontal axis with respect to the third link in the area of the other end thereof, the fourth link is mounted rotatably in the area of its other end relative to a second horizontal axis in the area of one of the two ends of the fifth link with respect to the fifth link G5 and the fifth link is mounted rotatably in the area of its other end relative to a third horizontal axis in the area of one of the two ends of the sixth link with respect to the sixth link, and the robot arm comprises the patient couch or a fastening device on which the patient couch is fastened.

The further object of the invention is fulfilled by a medical workstation featuring a medical device and the patient-positioning device according to the invention.

The medical workstation according to the invention is particularly provided for radiation therapy. The medical device is thus preferably a device to produce highly energized ionizing radiation, e.g. gamma radiation, X-ray radiation or even accelerated electrons, neutrons, protons or heavy ions. The device to produce highly energized ionizing radiation comprises, for example, a radiation source, which produces the highly energized ionizing radiation.

The robot arm can be part of a robot, which, in addition to the robot arm, comprises an electronic controller provided to control the movement of the robot arm. According to one variant of the patient-positioning device according to the invention, this comprises said robot.

The robot arm can comprises motors, in particular electric motors, which make the movement of the robot arm possible, at least indirectly controlled by the electronic controller.

It can also be provided for the robot arm to be manually movable. To do this, an input device connected to the electronic controller can be provided, for example, with which a person can make entries, based on which the electronic controller moves the robot arm according to the input. The position and orientation of the fastening device and therefore of the patient couch are thus accordingly arranged in space.

The medical device can feature its own electronic controller, which controls the normal operation of the medical device. The electronic controller of the medical device and the electronic controller of the robot can be arranged such that they can communicate with one another.

It can also be provided that the medical workstation features a shared electronic controller, which not only controls or is set to control the robot arm, but also controls or is set to control the normal operation of the medical device.

The robot arm according to the invention thus comprises the start link. It is preferably provided that the robot arm can be fastened and in particular screwed to a floor with the start link. The robot arm is preferably fastened, in particular screwed to the floor of the medical workstation with its start link. This allows for a relatively simple mounting of the robot arm or the patient-positioning device.

The start link is designed, for example, as a base plate, which is preferably as flat as possible.

The robot arm comprises, in addition to the start link, the first link, the second link and the third link, which are mounted rotatably relative to the three vertical axes. The first link, the second link and the third link thus extend in a horizontal direction and allow for a relatively flexible alignment of the patient couch in a horizontal direction.

The third link is preferably mounted on the second link and the second link on the first link.

In particular, the second link is shorter than the first link and/or the third link is shorter than the second link.

Following the third link are the fourth link, the fifth link and the sixth link, which are mounted rotatably with regard to the horizontal axes. These links thus allow the patient couch to be positioned aloft.

The sixth link can comprise the fastening device or the patient couch so that the robot arm comprises exactly six axes.

According to a preferred embodiment of the patient-positioning device according to the invention, the robot arm comprises, as one of the links, an end link, which comprises the fastening device or the patient couch. In this case, the sixth link is mounted rotatably in the area of one of its ends relative to the third horizontal axis with respect to a seventh axis of the robot arm in the area of the other end of the sixth link with respect to the sixth link.

The seventh axis preferably runs along a longitudinal axis or parallel to the longitudinal axis of the patient couch. It is thus possible to rotate the patient couch, for example, by a few degrees relative to its longitudinal extension relative to the floor. This can be advantageous, for example, when radiating a living being lying on the patient couch.

The seventh axis and the third horizontal axis preferably form a right angle.

One embodiment of the invention is illustrated with an example in the attached schematic drawings.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate exemplary embodiments of the invention and, together with a general description of the invention given above, and the detailed description given below, serve to explain the principles of the invention.

DETAILED DESCRIPTION

Figure 1:
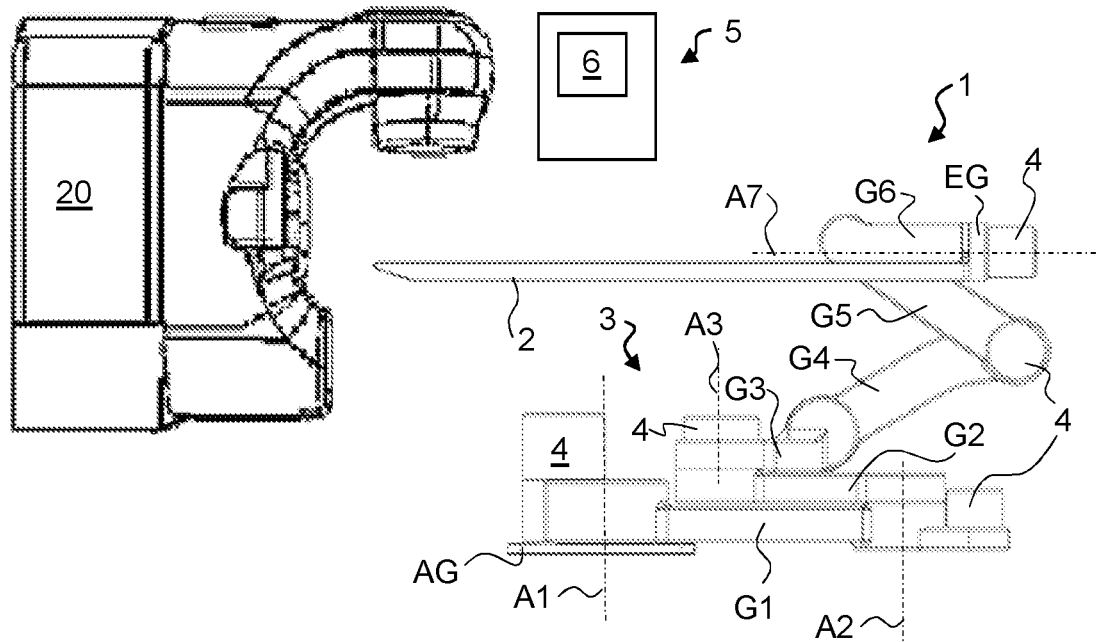
FIG. 1 shows a medical workstation with a patient-positioning device and a medical device.

FIG. 1 shows a side view of a medical workstation with a patient-positioning device 1 and a medical device 20. The medical workstation is provided in particular for radiation therapy.

Figure 2:
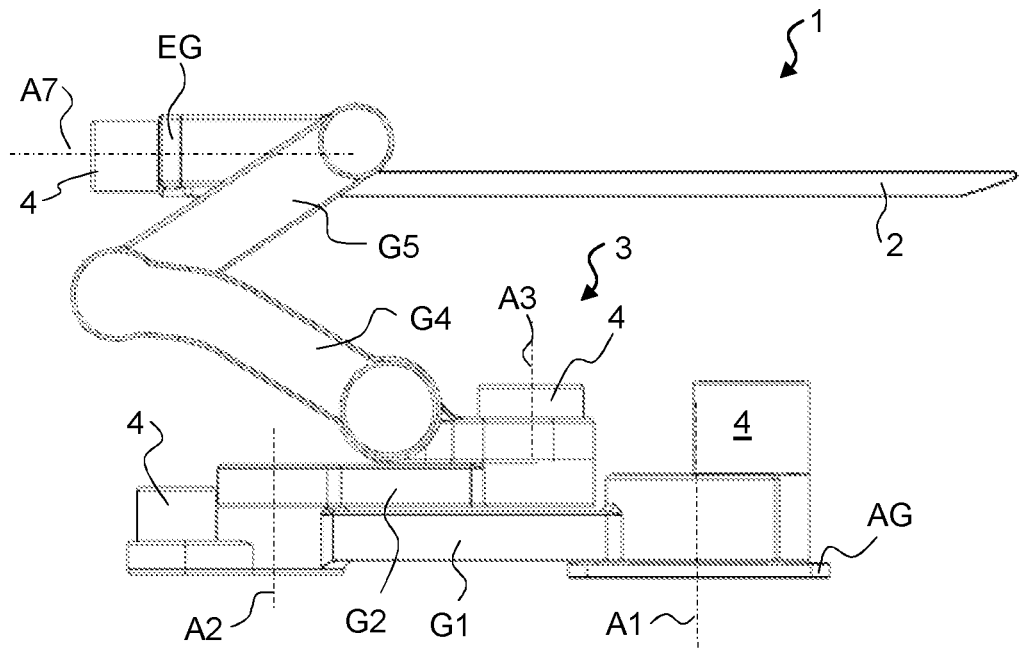
FIG. 2 shows a profile view of the patient-positioning device.
Figure 3:
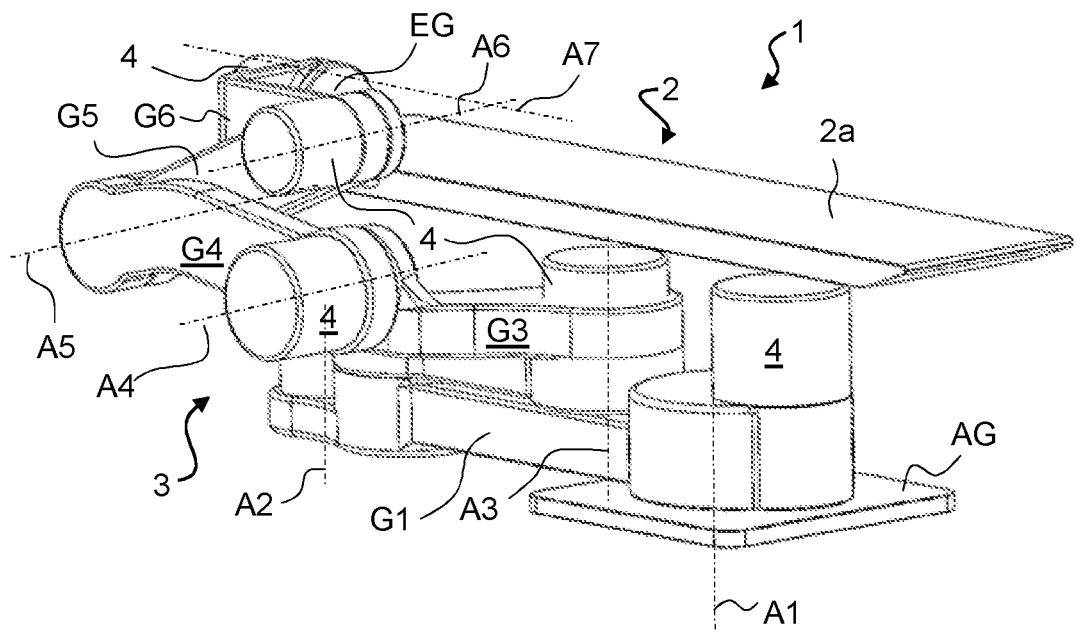
FIGS. 3-6 show various perspective views of the patient-positioning device.
Figure 4:
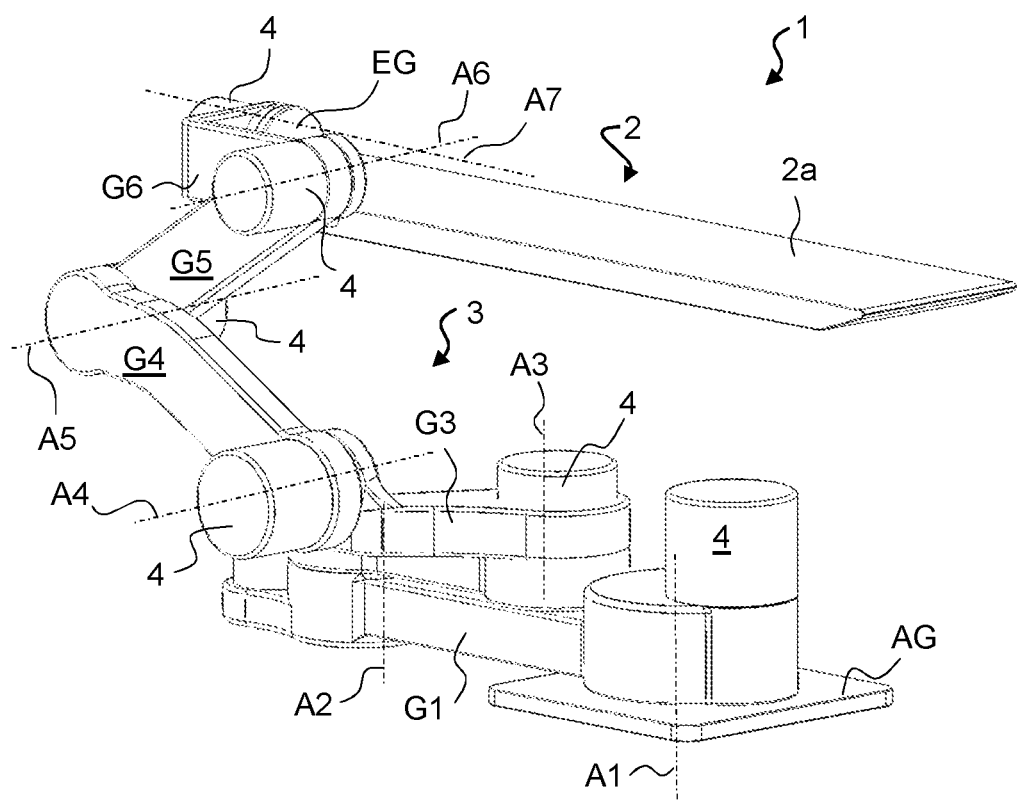
Figure 5:
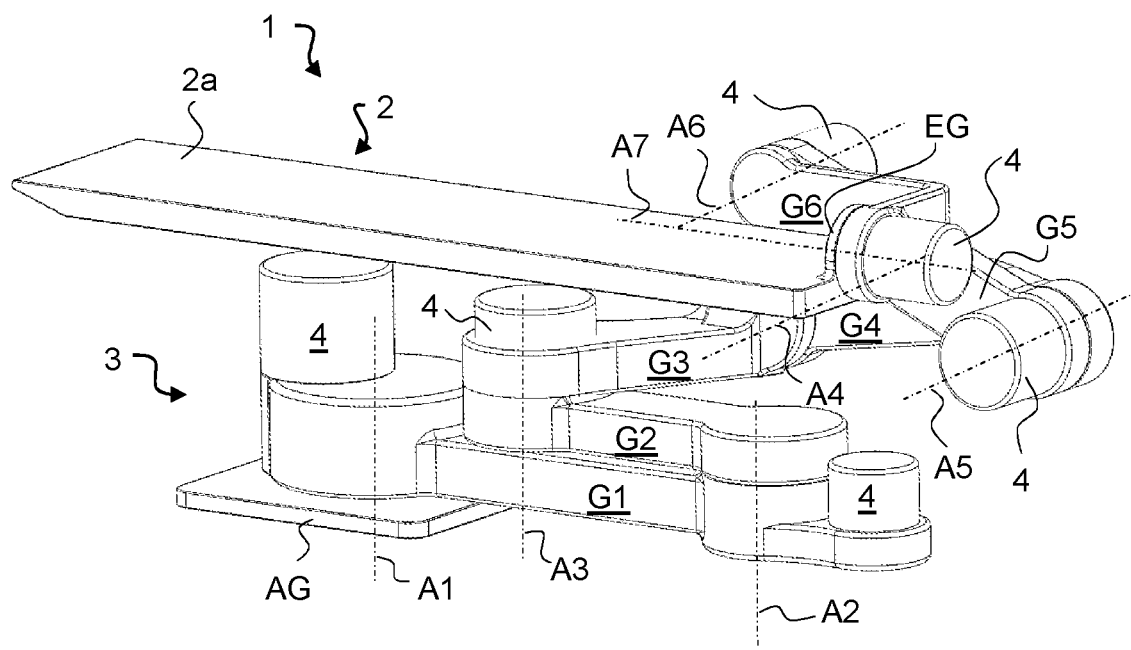
Figure 6:
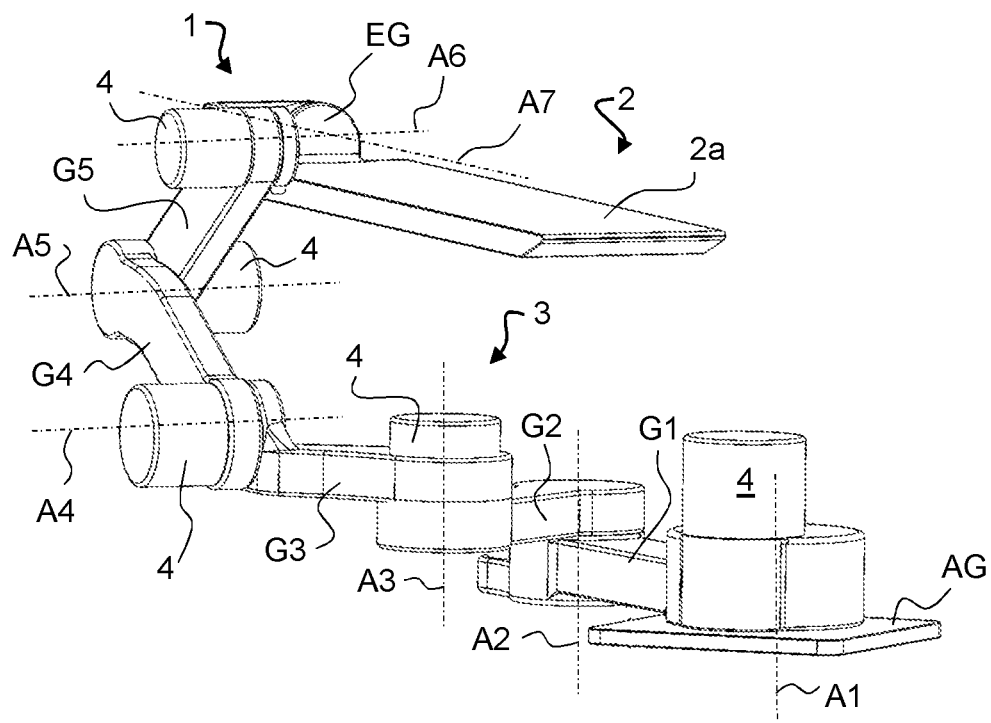

A further side view of the patient-positioning device 1 is show in FIG. 2 and various perspective views of the patient-positioning device 1 are shown in FIGS. 3 to 6.

In the case of the present embodiment, the medical device 20 is a device, previously known, in principle, by a person trained in the art, to produce highly energized ionizing radiation, e.g. gamma radiation, X-ray radiation or even accelerated electrons, neutrons, protons or heavy ions. The device to produce highly energized ionizing radiation comprises, for example, a radiation source, which produces the highly energized ionizing radiation.

The patient-positioning device 1 comprises in particular a patient couch 2, which is provided such that a living being not depicted may lie on it.

The patient-positioning device 1 comprises a robot arm 3, which comprises several links arranged one after another and mounted rotatably with respect to axes, e.g. with hinges. The robot arm 3 represents an open kinematic chain and thus comprises, as one of the links, a start link AG and an end link EG. The start link AG is, in the case of the present embodiment, a base plate, which is fastened to the floor. The start link AG embodied as a base plate is embodied as flat as possible. The start link AG can, however, also be embodied as a base, with which the robot arm 3 is fastened to the floor.

The end link EG comprises, for example, a fastening device, to which the patient couch 2 is fastened, so that this can be moved by the robot arm 3. In particular, the patient couch 2 is fastened in the area of one of its ends to the fastening device.

In the case of the present embodiment, however, it is provided that the end link EG comprises the patient couch 2.

The robot arm 3 comprises motors 4, in particular electric motors, with which the individual links of the robot arm 3 can be moved automatically, for example.

The electric motors 4 are, in particular, each a part of the electric power units, whose control elements or performance electrics can be mounted, for example, in or on the robot arm 3. In the case of the present embodiment, the control elements or performance electronics are mounted in a control box 5.

In particular, the robot arm 3 is part of a robot, which features, in addition to the robot arm 3, an electronic controller 6, which is mounted, for example, inside the control box 5.

The electronic controller 6 is connected to the electric power units in a way that is not represented.

A computer runs, for example, on the electronic controller 6 so that the electronic controller 6 may control the power units such that the position and orientation of the fastening device and thus of the patient couch 2 can be arranged in space. The electronic controller 6 can be set, if necessary, to regulate the power units of the robot, so in the present case, the term "control" should also comprise the term "regulate." If necessary, the electric power units are regulated electric power units.

It can also be provided that the robot arm 3 can be moved manually. To do this, an input device connected to the electronic controller 6 and not represented in greater detail can be provided, for example, with which a person can make entries, based on which the electronic controller 6 moves the robot arm 3 according to the input. The position and orientation of the fastening device and therefore of the patient couch 2 are thus accordingly arranged in space.

The medical device 20 can feature its own electronic controller not represented in greater detail, which controls the normal operation of the medical device 20. The electronic controller of the medical device 20 and the electronic controller 6 of the robot can be arranged such that they can communicate with one another.

It can also be provided that the medical workstation features a shared electronic controller so that the electronic controller 6 not only controls the robot arm 3, but also the normal operation of the medical device 20.

In the case of the present embodiment, the robot arm 3 features exactly seven axes.

The robot arm 3 features exactly three horizontal axes and three vertical axes. In particular, the robot arm 3 comprises a first vertical axis A1, a second vertical axis A2 and a third vertical axis A3, as well as a first horizontal axis A4, a second horizontal axis A5 and a third horizontal axis A6.

The robot arm 3 comprises in particular, as links, a first link G1, a second link G2, a third link G3, a fourth link G4, a fifth link G5 and a sixth link G6, which are mounted between the start link AG and the end link EG.

The first link G1 is mounted rotatably in the area of one of its two ends relative to the first vertical axis A1 with respect to the start link AG.

The first link G1 is mounted rotatably in the area of its other end relative to the second vertical axis A2 in the area of one of the two ends of the second link G2 with respect to the second link G2.

The second link G2 is mounted rotatably in the area of its other end relative to the third vertical axis A3 in the area of one of the two ends of the third link G3 with respect to the third link G3.

The fourth link G4 is mounted rotatably in the area of one of its ends relative to the first horizontal axis A4 with respect to the third link G3 in the area of the other end thereof.

The fourth link G4 is mounted rotatably in the area of its other end relative to the second horizontal axis A5 in the area of one of the two ends of the fifth link G5 with respect to the fifth link G5.

The fifth link G5 is mounted rotatably in the area of its other end relative to a third horizontal axis A6 in the area of one of the two ends of the six link G6 with respect to the sixth link G6.

In the area of the other end of the sixth link G6, the end link EG is mounted rotatably with respect to a seventh axis A7 of the robot arm.

The seventh axis A7 is oriented to run along the longitudinal axis or parallel to the longitudinal axis of the patient couch 2. It is thus possible to rotate the patient couch by a few degrees.

The seventh axis and the sixth axis A6 preferably form a right angle. The seventh axis A7 and the sixth axis A6 preferably intersect.

The first link G1, the second link G2 and the third link G3 thus extend in a horizontal direction.

In particular, the third link G3 is mounted on the second link G2 and the second link G2 on the first link G1. The third link G3 is preferably shorter than the second link G2.

It is also possible for the robot arm 3 not to comprise the seventh axis A7 and the end link EG, but instead for the sixth link G6 to comprise the patient couch 2 or the sixth link G6 to comprise the fastening device to fasten the patient couch 2.

While the present invention has been illustrated by a description of various embodiments, and while these embodiments have been described in considerable detail, it is not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

What is claimed is:

1. A patient-positioning apparatus, comprising:
a robot arm provided for moving a patient couch, the robot arm comprising a plurality of serially arranged links mounted rotatably with respect to one another about respective axes, wherein the links of the robot arm include a start link, a first link, a second link, a third link, a fourth link, a fifth link, and a sixth link, wherein:
the first link is mounted at a first end to the start link for rotation with respect to the start link about a first vertical axis,
the first link is mounted at a second end to a first end of the second link for rotation with respect to the to the second link about a second vertical axis,
the second link is mounted at a second end to a first end of the third link for rotation with respect to the third link about a third vertical axis,
the fourth link is mounted at a first end to a second end of the third link for rotation with respect to the third link about a first horizontal axis,
the fourth link is mounted at a second end to a first end of the fifth link for rotation with respect to the fifth link about a second horizontal axis, and
the fifth link is mounted at a second end to the sixth link for rotation about a third horizontal axis; and
wherein the robot arm further comprises the patient couch or a fastening device for supporting the patient couch on the robot arm;
whereby the serially arranged links enable flexible alignment of the patient couch in a horizontal direction within a compact space.

2. The patient-positioning apparatus of claim 1, wherein the start link is configured to be fastened to a floor.

3. The patient-positioning apparatus of claim 2, wherein the start link is configured to be screwed to the floor.

4. The patient-positioning apparatus of claim 1, wherein the third link is mounted on the second link and positioned vertically above the second link, and the second link is mounted on the first link and positioned vertically above the first link.

5. The patient-positioning apparatus of claim 1, wherein at least one of:
the second link is shorter in length than the first link; or
the third link is shorter in length than the second link.

6. The patient-positioning apparatus of claim 1, wherein the sixth link comprises the patient couch or the fastening device for supporting the patient couch on the robot arm.

7. The patient-positioning apparatus of claim 1, wherein the robot arm further comprises, as one of the serially arranged links, an end link rotatably mounted relative to the sixth link about a seventh axis of the robot arm, the end link defining the patient couch or comprising a fastening device for supporting the patient couch on the robot arm.

8. The patient-positioning apparatus of claim 7, wherein at least one of:
the seventh axis extends along a longitudinal axis of the patient couch, or parallel to the longitudinal axis of the patient couch; or
the seventh axis and the third horizontal axis form a right angle.

9. The patient-positioning apparatus of claim 1, further comprising an electronic controller configured to control movement of the robot arm.

10. A medical workstation, comprising:
a medical device; and
a patient-positioning apparatus according to claim 1, the patient positioning apparatus positioned proximate the medical device for moving the patient couch relative to the medical device.

* * * * *